United States Patent [19]

Owens et al.

[11] Patent Number: 5,494,926
[45] Date of Patent: Feb. 27, 1996

[54] 2/3-(HETEROCYCLIC ALKYL AMINO)-1-(SUBST.-PHENYL-METHOXY)-ETHANES/PROPANES AS TACHYKININ-RECEPTOR ANTAGONISTS

[75] Inventors: Andrew P. Owens, Rushden; Martin Teall, Stansted; Brian Williams, Great Dunmow, all of Great Britain

[73] Assignee: Merck Sharp & Dohme Ltd., Hoddesdon, England

[21] Appl. No.: 338,484

[22] Filed: Nov. 18, 1994

[30] Foreign Application Priority Data

May 27, 1992 [GB] United Kingdom ............ 9211193

[51] Int. Cl.$^6$ .......... A61K 31/42; C07D 263/10
[52] U.S. Cl. .......... 514/364; 546/176; 546/334; 548/131; 548/252; 548/253; 548/263.2; 548/267.2; 548/319.1; 548/319.5; 548/320.1
[58] Field of Search .......... 548/131, 252, 548/253, 263.2, 267.2, 319.1, 319.5, 320.1; 514/364, 369, 381, 383, 384, 389

[56] References Cited

U.S. PATENT DOCUMENTS 5,245,080  9/1993  Aubard et al. .

FOREIGN PATENT DOCUMENTS

| 0194464A1 | 9/1986 | European Pat. Off. . |
|---|---|---|
| 0297782 | 1/1989 | European Pat. Off. . |
| 0330940 | 9/1989 | European Pat. Off. . |
| 0394989A3 | 10/1990 | European Pat. Off. . |
| 0415413A1 | 3/1991 | European Pat. Off. . |
| 0522808A2 | 1/1993 | European Pat. Off. . |
| 2035535 | 1/1971 | Germany . |
| 2054588 | 2/1981 | United Kingdom . |
| WO91/12266 | 8/1991 | WIPO . |

OTHER PUBLICATIONS

Curran et al. "The Total Synthesis fo Nocardin A", The Jour. of Antibiotics, vol. XXXV, No. 3 pp. 329–334 1982.
Pascaud et al. "Effects of Fedotozine on Gastrointestinal Motility in Dogs: Mechanism of Action and Related Pharmacokinetics", J. Pharm Pharmacol. 1990, vol. 42, pp. 546–552.
March, J. Advanced Organic Chemistry: Reactions, Mechanisms, and Structure. McGraw–Hill Book Co., New York, 1968.

*Primary Examiner*—Jacqueline Haley
*Attorney, Agent, or Firm*—Robert J. North; Melvin Winokur

[57] ABSTRACT

Compounds of formula (I), and salts and prodrugs thereof, wherein Q represents phenyl or benzhydryl; X and Y each represent H or X and Y together form a group =O; Z is O, S or $NR^8$ ($R^8$ is H or $C_{1-6}$alkyl); $R^1$ is H, optionally substituted $C_{1-6}$alkyl, phenyl($C_{1-4}$alkyl), $C_{2-6}$alkylene, $COR^a$, $COOR^a$, $CONHR^a$, $COC_{1-4}$alkyl$NR^aR^b$, or $CONR^aC_{1-4}$alkyl$CONR^aR^b$; $R^2$ is $C_{1-4}$alkyl substituted by an optionally substituted aromatic heterocycle; $R^3$ is H, $C_{1-6}$alkyl or $C_{2-6}$alkenyl; $R^4$ is H, $C_{1-6}$alkyl or optionally substituted phenyl; $R^5$ represents optionally substituted phenyl; and q is 0, 1, 2 or 3; are tachykinin antagonists useful in therapy.

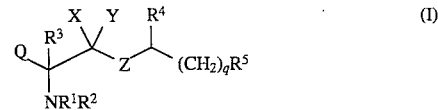

15 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Arg Pro Lys Pro Gln Gln Phe Phe Gly Leu Met
1               5                   10

( 2 ) INFORMATION FOR SEQ ID NO:2:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

His Lys Thr Asp Ser Phe Val Gly Leu Met
1               5                   10

( 2 ) INFORMATION FOR SEQ ID NO:3:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Asp Met His Asp Phe Phe Val Gly Leu Met
1               5                   10

2/3-(HETEROCYCLIC ALKYL AMINO)-1-(SUBST.-PHENYL-METHOXY)-ETHANES/PROPANES AS TACHYKININ-RECEPTOR ANTAGONISTS

This application is a National Stage Application of PCT/GB93/01072 filed May 25, 1993, published Dec. 9, 1993 as WO/93/24465.

This invention relates to a class of compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:

Arg—Pro—Lys—Pro—Gln—Gln—Phe—Phe—Gly—Leu—Met—NH$_2$ (Seq. ID No. 1)

Neurokinin A:

His—Lys—Thr—Asp—Ser—Phe—Val—Gly—Leu—Met—NH$_2$ (Seq. ID No. 2)

Neurokinin B:

Asp—Met—His—Asp—Phe—Phe—Val—Gly—Leu—Met—NH$_2$ (Seq. ID No. 3)

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], and immunoregulation [Lotz et al Science (1988) 241 1218–21 and Kimball et al, J. Immunol. (1988) 141 (10) 3564–9]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflx sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

European patent application no. 0 194 464 discloses compounds of formula (A):

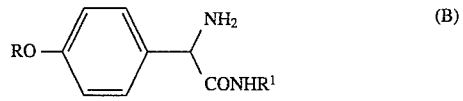

wherein:
R$^1$ is loweralkyl, arylloweralkyl or optionally substituted phenyl;
R$^2$ is inter alia phenyl;
R$^3$ is inter alia H or loweralkyl;
R is inter alia arylloweralkyl; and
n is inter alia 1.

The compounds are said to have anticonvulsant properties.

German patent application no. 28 51 435 discloses compounds of formula (B):

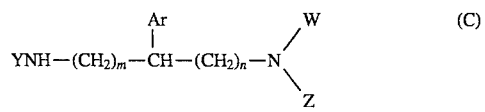

wherein:
R is H or CH$_3$; and
R$^1$ is inter alia a loweralkyl group substituted by an optionally substituted phenyl group.

The compounds are said to be useful in heart disease, obesity and diabetes.

Canadian patent application no 2,029,338 discloses compounds of formula (C):

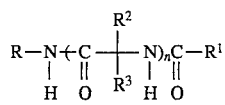

wherein
Ar is inter alia phenyl;
m is inter alia zero;
Y is

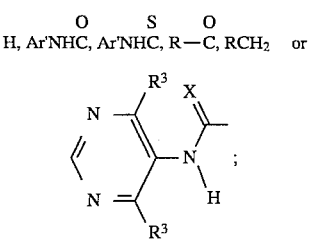

n is inter alia 1;
W is inter alia H or C$_{1-20}$alkyl; and
Z is inter alia R-CH$_2$, where R is inter alia optionally substituted phenyl.

The compounds are said to be ACAT inhibitors useful in lowering blood cholesterol levels.

British patent application no. 2054588 discloses compounds of formula (D):

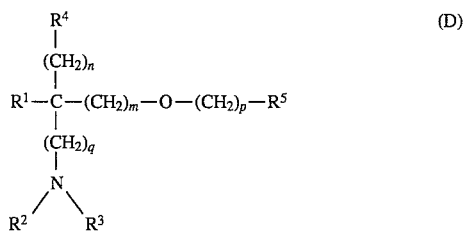

wherein
R$^1$ is C$_{1-10}$ alkyl;

$R^2$ and $R^3$ are H or $C_{1-10}$alkyl;
$R^4$ is inter alia optionally substituted phenyl;
$R^5$ is inter alia optionally substituted phenyl;
n is inter alia zero;
m is inter alia 1;
p is inter alia 1; and
q is inter alia zero.

The compounds are said to have anti-spasmolytic, anaesthetic and analgesic activity.

There is no prior art disclosure of the amine substitution of the compounds of the present invention.

The present invention provides a compound of formula (I), or a salt or prodrug thereof:

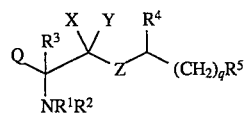

wherein

Q represents optionally substituted phenyl or optionally substituted benzhydryl;

X and Y each represent H or X and Y together form a group =O;

Z represents O, S or $NR^8$, where $R^8$ represents H or $C_{1-6}$alkyl;

$R^1$ represents H, $C_{1-6}$alkyl optionally substituted by hydroxy, cyano, $COR^a$, $COOR^a$, $CONR^aR^b$, $COC_{1-4}$alkyl-$NR^aR^b$, $CONR^aC_{1-4}$alkyl$CONR^aR^b$ or $NR^aR^b$, (where $R^a$ and $R^b$ each independently represent H, $C_{1-6}$alkyl or $C_{0-4}$alkylphenyl optionally substituted in the phenyl ring by one or more of $C_{1-6}$alkyl, $C_{1-6}$alkoxy, halo and trifluoromethyl), phenyl($C_{1-4}$ alkyl), (optionally substituted by one or more of $C_{1-6}$alkyl, $C_{1-6}$alkoxy, halo and trifluoromethyl in the phenyl ring), $C_{2-6}$alkylene, $COR^a$, $COOR^a$, $CONHR^a$, $COC_{1-4}$alkyl$NR^aR^b$, or $CONR^aC_{1-4}$alkyl$CONR^aR^b$ where $R^a$ and $R^b$ are as previously defined;

$R^2$ represents $C_{1-4}$alkyl substituted by an optionally substituted aromatic heterocycle;

$R^3$ represents H, $C_{1-6}$alkyl or $C_{2-6}$alkyenyl;

$R^4$ represents H, $C_{1-6}$alkyl or phenyl (optionally substituted by one or more of $C_{1-6}$alkyl, $C_{2-6}$alkenyl, $C_{2-6}$alkynyl, halo, cyano, nitro, trifluoromethyl, trimethylsilyl $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$alkyl, phenyl or trifluoromethyl);

$R^5$ represents phenyl optionally substituted by one or more $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined; and
q is 0, 1, 2 or 3.

As used herein, the definition of each expression, when it occurs more than once in any structure, is intended to be independent of its definition elsewhere in the same structure.

The alkyl, alkenyl and alkynyl groups referred to with respect to any of the above formulae may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where Q represents substituted phenyl or benzhydryl, suitable substituents include $C_{1-6}$alkyl, $C_{2-6}$alkenyl, $C_{2-6}$alkynyl, halo, cyano, nitro, trifluoromethyl trimethylsilyl, $SR^c$, $SOR^c$, $SO_2R^c$, $OR^c$ $NR^cR^d$, $NR^cCOR^d$, $NR^cCOOR^d$, $COOR^c$ or $CONR^cR^d$, where $R^c$ and $R^d$ are as above defined. One or more substituents may be present and each may be located at any available ring position.

Preferably Q is unsubstituted phenyl or unsubstituted benzhydryl.

Preferably X and Y each represents H.

Preferably Z represents O.

Suitable values for the group $R^1$ include H, $C_{1-6}$alkyl, especially methyl, ethyl, propyl, and cyclopropylmethyl, $C_{1-6}$alkyl substituted by, for example, cyano, hydroxy, $NH_2$, $CO_2$, $C_{1-6}$alkyl, $CONH_2$ and $CONR^aCH_2CONR^aR^b$, especially $CONHCH_2CONH_2$, $COC_{1-4}$alkyl$NR^aR^b$, especially $COCH_2NR^aR^b$, such as $COCH_2NH_2$ and $C_{1-6}$ alkenyl, especially allyl and formyl. Preferably $R^1$ is H or $C_{1-6}$alkyl, such as $C_{1-4}$alkyl, for example methyl, ethyl or n-propyl.

When $R^2$ represents $C_{1-4}$alkyl substituted by a substituted aromatic heterocycle, suitable substituents in the heterocyclic ring include one or more of $C_{1-6}$alkyl, $C_{1-6}$alkoxy, phenyl, oxo, thioxo, halo, trifluoromethyl, $NR^cR^d$, $NR^c$-$COR^d$, $CONR^cR^d$, $C_2R^c$, $SR^c$, $SO_2R^c$ and $CH_2OR^c$ where $R^c$ and $R^d$ are as previously defined. Preferred substituents include methyl, oxo, thioxo and amino. Particularly preferred substituents are oxo and $NH_2$.

Suitable values for the heteroaromatic moiety of $R^2$ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted.

Preferably the heterocyclic moiety of $R^2$ represents a substituted or unsubstituted 5- or 6-membered nitrogen containing aromatic heterocycle such as for example oxazolyl, oxadiazolyl, tetrazolyl, thiazolyl, thiadiazolyl, triazolyl, pyrazinyl, pyridyl, pyrimidinyl, pyridazinyl, imidazolyl or triazinyl. More preferably the heterocyclic moiety of $R^2$ represents optionally substituted oxadiazolyl, imidazolyl, triazolyl, or tetrazolyl.

Particularly preferred are compounds according to the invention wherein the heterocyclic moiety of $R^2$ represents 5-(3-aminooxadiazolyl), unsubstituted triazolyl or triazolyl substituted by oxo or thioxo.

It will be appreciated that, when the heterocyclic moiety of $R^2$ is substituted by an oxo or thioxo substituent, different tautomeric forms are possible so that the substituent may be represented as =O or —OH, or =S or —SH, respectively. For the avoidance of doubt, all such tautomeric forms are embraced by the present invention.

Suitable values for the $C_{1-4}$alkyl moiety of $R^2$ include $CH_2$, $CH(CH_3)$ and $CH_2CH_2$. Preferably the $C_{1-4}$alkyl moiety of $R^2$ is $CH_2$ or $CH(CH_3)$, more preferably $CH(CH_3)$.

Suitable values for the group $R^3$ include H and methyl, preferably H.

Preferably $R^4$ represents H or $C_{1-4}$alkyl, especially methyl.

Suitably q is zero, 1 or 2, preferably zero.

Preferably $R^5$ represents substituted phenyl. Suitable phenyl substituents include $C_{1-6}$alkyl such as methyl, ethyl, i-propyl, i-butyl, t-butyl and cyclopropyl, $C_{2-6}$alkenyl such as vinyl, $C_{1-6}$alkoxy such as methoxy, ethoxy and i-propoxy, phenoxy, amino, carboxamido, carbonylmethoxy, trimethylsilyl, nitro, cyano, bromo, chloro, fluoro, iodo and trifluoromethyl. Preferably $R^5$ represents phenyl substituted by one or more groups selected from $C_{1-4}$alkyl, such as methyl and t-butyl, trifluoromethyl and halo such as bromo, chloro, fluoro and iodo. Preferably $R^5$ represents 3,5-disubstituted phenyl. A particularly preferred value for $R^5$ is 3,5-bistrifluoromethylphenyl.

A preferred sub-group of compounds according to the invention is represented by formula (Ia)

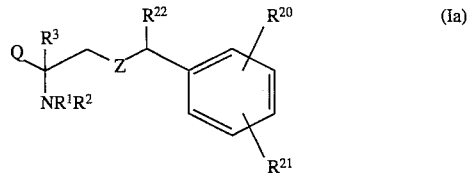

wherein Q, $R^1$, $R^2$, $R^3$ and Z are as defined for formula (I) above;

$R^{20}$ and $R^{21}$ each independently represent H, $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined;

$R^{22}$ represents H or methyl; and salts and prodrugs thereof.

Particularly preferred are compounds of formula (Ia) wherein $R^{20}$ and $R^{21}$ are other than H and are located in the 3- and 5-positions. Most preferably $R^{20}$ and $R^{21}$ each represent $C_{1-4}$alkyl, halo or trifluoromethyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable nontoxic acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when $R^1$ is other than H, the nitrogen atom to which it is attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of Examples 1–10, for example, were found to have $IC_{50}$ values less than 100 nM.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinoma such as small cell lung cancer; respiratory diseases such as chronic obstructive airways disease, bronchopneumonia, bronchospasm and asthma; inflammatory diseases such as inflammatory bowel disease, irritable bowel syndrome, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like, and proliferative vitreoretinopathy; cutaneous diseases such as contact dermatitis, atropic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as cystitis and bladder detrusor hyperreflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg of a compound of formula (I) per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

According to one general process (A), the compounds according to the invention may be prepared by reaction of a compound of formula (II)

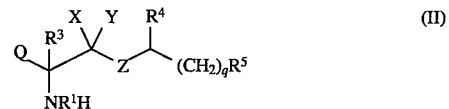

(II)

wherein Q, $R^1$, $R^3$, $R^4$, $R^5$, q, X, Y and Z are as defined for formula (I), with a reagent suitable to introduce the group $R^2$, for example, a halide of formula $R^2$-Hal, where Hal represents halo, such as chloro, bromo or iodo, in the presence of a base.

Suitable bases of use in the reaction include inorganic bases such as alkali metal carbonates, for example, potassium carbonate.

Conveniently the reaction is effected in a suitable organic solvent, such as an amide, for example, dimethyl formamide.

According to a second process (B) compounds of formula (I) wherein $R^2$ represents $C_{1-4}$alkyl substituted by optionally substituted 5-oxadiazolyl may be prepared by reaction of a compound of formula (III) with a compound of formula (IV):

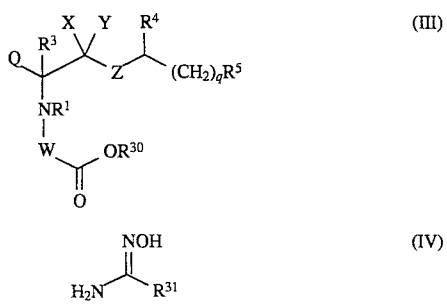

wherein Q, $R^1$, $R^3$, $R^4$, $R^5$, q, X, Y and Z are as defined for formula (I), W represents $C_{1-4}$alkylidene, $R^{30}$ represents an alkyl group and $R^{31}$ represents H, $C_{1-6}$alkyl, $C_{1-6}$alkoxy, halo, $NR^cR^d$ or $NR^cCOR^d$, where $R^c$ and $R^d$ are as previously defined, in the presence of a base.

Suitable bases of use in the reaction include alkali metals, such as, for example, sodium, and alkali metal hydrides, such as, for example, sodium hydride.

The reaction is conveniently effected in a suitable organic solvent. Which solvents will be appropriate will depend on the nature of the base used. For example, where the base used is an alkali metal, suitable solvents will include alcohols, for example, ethanol, whereas where the base used is an alkali hydride, suitable solvents will include ethers, for example, tetrahydrofuran.

Preferably the reaction is conducted at elevated temperature, such as the reflux temperature of the chosen solvent.

According to a further process, (C), compounds of formula (I) wherein the heterocyclic moiety of $R^2$ represents tetrazolyl may be prepared from intermediates of formula (V):

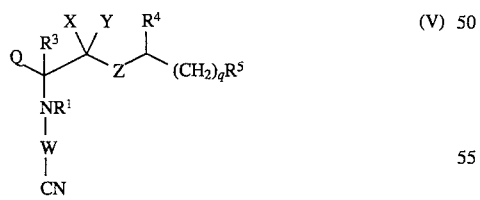

wherein Q, $R^1$, $R^3$, $R^4$, $R^5$, q, X, Y, W and Z are as defined for formula (III) by treatment with an alkali metal azide, such as sodium azide.

The reaction is conveniently effected in a high boiling organic solvent, such as, for example, N-methylpyrrolidinone.

According to a further process, (D), compounds of formula (I) wherein the heteroaromatic moiety of $R^2$ represents thiazolyl may be prepared from intermediates of formula (VI):

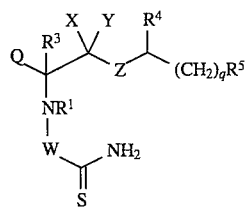

wherein Q, $R^1$, $R^3$, $R^4$, $R^5$, q, X, Y, W and Z are as defined for formula (III), by reaction with a compound of formula Hal-$CH_2C(O)$-$R^{60}$, where Hal represents halo, such as bromo, chloro or iodo, and $R^{60}$ represents H or a suitable substituent such as $C_{1-6}$alkyl.

The reaction is conveniently effected in a suitable organic solvent, such as a ketone, for example, acetone, or an alcohol, for example, methanol, or a mixture of solvents, preferably at elevated temperature, such as the reflux temperature of the chosen solvent.

According to a further process, (E), compounds of formula (I) wherein the heteroaromatic moiety of $R^2$ represents thioxotriazolyl may be prepared from intermediates of formula (VII)

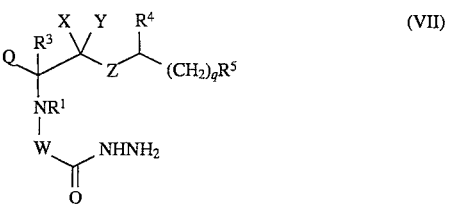

wherein Q, $R^1$, $R^3$, $R^4$, $R^5$, q, X, Y, W and Z are as defined for formula (III), by reaction with a compound of formula $R^{61}NCS$, wherein $R^{61}$ represents H or a suitable substituent such as $C_{1-6}$alkyl, in the presence of a base.

Suitable bases of use in the reaction include organic bases such as, for example, 1,8-diazabicyclo[5.4.0]undec-7-ene (DBU). The reaction is conveniently effected in a suitable organic solvent, such as alcohol, e.g. butanol.

According to a further process, (F), compounds of formula (I) wherein the heteroaromatic moiety of $R^2$ represents unsubstituted or substituted triazolyl may be prepared by reaction of intermediates of formula (II) with a compound of formula (VIII):

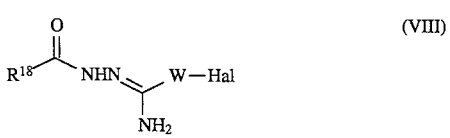

wherein W and Hal are as previously defined and $R^{18}$ is H or a group suitable as a substituent of the triazole ring, or convertible to such a group under the reaction conditions, in the presence of a base.

Suitable bases of use in the reaction include alkali metal carbonates, such as, for example, potassium carbonate.

Suitably $R^{18}$ represents H, $OCH_3$ (which is converted to an oxo substituent under the reaction conditions) or $CONH_2$.

The reaction is conveniently effected in an anhydrous organic solvent, such as, for example, anhydrous dimethylformamide, preferably at elevated temperature, such as about 140° C.

According to a further process, (G), compounds of formula (I) wherein the heteroaromatic moiety of $R^2$ represents substituted or unsubstituted 1,3,5-triazine may be prepared by reaction of intermediates of formula (IX):

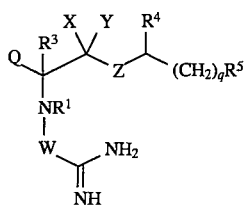

wherein Q, $R^1$, $R^3$, $R^4$, $R^5$, q, X, Y, W and Z are as defined for formula (III), with substituted or unsubstituted 1,3,5-triazine.

The reaction is conveniently effected in a suitable organic solvent, such as acetronitrile, at elevated temperature, such as 80°–90° C., preferably about 82° C.

According to a further process, (H), compounds of formula (I) wherein the heteroaromatic moiety of $R^2$ represents substituted or unsubstituted 1,2,5-triazine may be prepared by reaction of an intermediate of formula (X) with a dicarbonyl compound of formula (XI):

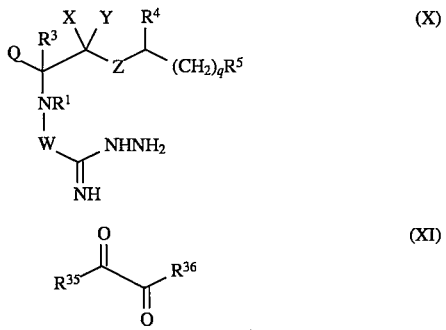

wherein Q, $R^1$, $R^3$, $R^4$, $R^5$, q, X, Y, W and Z are as defined for formula (III) and $R^{35}$ and $R^{36}$ each independently represent H or a suitable substituent such as $C_{1-6}$alkyl, e.g. methyl.

The reaction is conveniently effected in a suitable organic solvent, such as an ether, e.g. tetrahydrofuran, conveniently at ambient temperature.

Further details of suitable procedures will be found in the accompanying Examples.

Compounds of formula (I) may also be prepared from other compounds of formula (I) using suitable interconversion procedures. Suitable interconversion procedures are described in the accompanying Examples, or will be readily apparent to those skilled in the art.

Intermediates of formula (II) may be prepared as described in published International patent applications nos. 93/01160 and 93/01165.

Intermediates of formula (III) may be prepared from intermediates of formula (II) by reaction with a compound of formula $HalWCO_2R^{30}$, where Hal represents halo such as chloro, bromo or iodo and W and $R^{30}$ are as above defined, in the presence of a base. Suitable bases include tertiary amines, for example, triethylamine. Conveniently the reaction is effected in a suitable organic solvent, such as an ether, for example, tetrahydrofuran, at elevated temperature, such as the reflux temperature of the solvent.

Intermediates of formula (IV) are commercially available or may be prepared from commercially available materials by conventional procedures well-known to those skilled in the art.

Intermediates of formula (V) may be prepared from intermediates of formula (II) by reaction with a compound of formula Hal-W-CN, wherein Hal is halo such as bromo, chloro or iodo and W is as previously defined.

Intermediates of formula (VI) may be prepared from intermediates of formula (V) by treatment with an alkylthioamide, such as, for example, thioacetamide.

Intermediates of formula (VII) may be prepared from intermediates of formula (III) by treatment with hydrazine. The reaction is conveniently effected in a suitable organic solvent, such as an alcohol, for example, ethanol, at elevated temperature.

Compounds of formula (VIII) may be prepared as described in *J. Med. Chem*, 27, (1984), 849.

Intermediates of formula (IX) may be prepared from intermediates of formula (II) by reaction with a compound of formula Hal-W-C(NH)$NH_2$, where Hal and W are as previously defined.

Intermediates of formula (X) may be prepared from intermediates of formula (II) by reaction with a compound of formula Hal-W-C(NH)NHNH-Boc, wherein Hal and W are as previously defined and Boc stands for t-butoxycarbonyl, followed by deprotection under acidic conditions.

Compounds of formula (XI) are commercially available or may be prepared from commercially available compounds by known methods.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

((3-Amino-1,2,4-oxadiazol-5-yl) methyl ammonium)-1-((3'5'-bis(trifluoromethyl)phenyl)methyloxy)-3,3-diphenyl-pronane-bis oxalate salt a) To a solution of diphenylmethyleneiminoacetonitrile (44g), benzyltrimethyl ammonium chloride (4.4g) and sodium hydroxide (48.4g) in toluene (40ml) and water (90ml) was added bromodiphenylmethane (149g) at 0° C. After the solution had been stirred at room temperature for 5h a mixture of water (200ml), ethyl acetate (40ml) and hexane (160ml) was added. The solution was filtered and the residue washed with ethyl acetate/hexane and dried in vacuo to give 3,3-diphenyl-2-(diphenylmethyleneimino)prop-rionitrile 47.6g. $^1$H NMR (360MHz, $CDCl_3$) δ 7.5-6.87

(20H, m, aryl), 4.8 (1H, d, J= 8.85Hz), 4.69 (1H, d, J=9.2Hz). An analytical sample was recrystallised from ethyl acetate/hexane mp=152°–153° C.

b) 3,3-Diphenyl-2-(diphenylmethyleneimino)proprionitrile (Example 1a, 46.7g) was heated in a solution of 5.5M-hydrochloric acid (200ml) at reflux for 48h. The solid which crystallised from the cooled solution was removed by filtration, washed with diethyl ether and dried to give β,β-diphenylalanine hydrochloride 21g. $^1$H NMR (250MHz, DMSO $d_6$) d 8.6 (3H, vbs), 7.6-7.1 (10H, m), 4.8 (1H, d, J=10.4Hz), 4.4 (1H, d, J=10.4Hz).

c) To a solution of 1M-lithium aluminium hydride in diethyl ether (40ml) was added β,β-diphenylalanine hydrochloride (3.70g, Example 1b) over a period of 1h. The solution was heated at reflux for 1h, cooled to room temperature and to the solution was cautiously added 2M-sodium hydroxide (40ml). After filtering the solution through Celite, the residue was washed with ethyl acetate and the organic phase of the combined filtrates was washed with water, saturated brine and dried (MgSO$_4$). The solid which formed on removal of the solvent in vacuo was washed with hexane to give 2-amino-3,3-diphenylpropan-1-ol 2.52g, mp 107°–8° C. $^1$H NMR (360MHz, CDCl$_3$) d 7.36-7.14 (10H, m), 3.79 (1H, d, J=10.5Hz), 3.6 (1H, m), 3.57 (1H, dd, J=10.7Hz and 3.3Hz), 3.31 (1H, dd, J=10.7Hz and 6.7Hz), m/z (CI$^+$) 228 (M+H).

d) A solution of 2-amino-3,3-diphenylpropan-1-ol (2.3g, Example 1c) and di-t-butyldicarbonate (2.65g) in dichloromethane (25ml) was stirred at room temperature for 1h. The solid which formed on removal of the solvent was recrystallized from diethyl ether to give 2-t-butoxycarbonylamino-3,3-diphenylpropan-1-ol (2.85g, mp 95°–96° C. $^1$H NMR (250MHz, CDCl$_3$) δ 7.34-7.15 (10H, m), 4.58 (1H, bd), 4.48 (1H, m), 4.1 (1H, d, J=10.6Hz), 3.67 (1H, dd, J= 11.13Hz and 3.11Hz), 3.5 (1H, dd, J=11.3Hz and 4.45Hz), 1.31 (9H, s).

e) To a cooled solution (0° C.) of 2-t-butoxycarbonylamino- 3,3-diphenylpropan-1-ol (2.04g, Example 1d) in tetrahydrofuran (50ml) and dimethylformamide (10ml) was added sodium hydride (0.187g, 80% suspension in oil) over 15 minutes. After an additional 10 minutes 3,5-bis(trifluoromethyl)benzyl bromide (1.14ml) was added and the solution stirred at room temperature for 16h. The solvent was removed in vacuo and the residue partitioned between CH$_2$Cl$_2$ and water. After washing the organic phase with saturated brine and drying (MgSO$_4$), the solvent was removed in vacuo and the residue chromatographed on silica gel in ethyl acetate/hexane (0:100 to 50:50) to give 2-t-butoxycarbonylamino-1-((3',5'-bis(trifluoromethyl)phenyl) methyloxy)3,3-diphenylpropane, 2.92g.

f) A solution of 2-t-butoxycarbonylamino- 1-((3',5'-bis (trifluoromethyl)phenyl)methyloxy)-3,3-diphenylpropane (2.92g, Example 1e) in trifluoroacetic acid (20ml) was evaporated after 10 minutes. A solution of the residue in CH$_2$Cl$_2$ was washed with 10% aqueous Na$_2$CO$_3$, water, saturated brine and dried (MgSO$_4$). Removal of the solvent in vacuo gave 2-amino-1-((3',5'-bis(trifluoromethyl)phenyl)methyloxy)-3,3-diphenylpropane.

g) To a solution of 2-amino-1-((3',5'-bis(trifluoromethyl) phenyl)methyloxy)-3,3-diphenylpropane (5.0g, Example 1f) and anhydrous K$_2$CO$_3$ (2.3g) in dimethylformamide (30ml) was added methyl bromoacetate (1.2ml). The solution was heated to 70° C. for 2 hours, cooled to ambient temperature and diluted by addition of water (200ml) and ethyl acetate (200ml). The organic phase was washed with water, saturated brine and dried (MgSO$_4$). After removal of the solvent in vacuo, the residue was chromatographed on silica gel eluting with ethyl acetate/hexane (5:95 to 20:80) to give 1-((3',5'-bis(trifluoromethyl) phenyl)methyloxy)-2-((carboxamido)methyl)amino-3,3-diphenylpropane, 2.91g.

h) To a solution of sodium ethoxide (0.78g) in ethanol (10ml) was added molecular sieves (0.5g, A4) and a suspension of hydroxyguanidine hemisulfate hemihydrate (1.8g) in ethanol (10ml). After 1 hour a solution of 1-((3', 5'-bis (trifluoromethyl)phenyl)methyloxy)-2-((carboxamido)methyl) amino-3,3-diphenylpropane (Example 1g, 0.6g) in ethanol (10ml) was added and the suspension heated at 100° C. for 2 hours. The suspension was filtered and the filtrate evaporated to dryness. The residue was partitioned between CH$_2$Cl$_2$ and water and the organic phase dried (MgSO$_4$) and evaporated. The residue was purified on silica gel eluting with increasing concentrations of methanol (1% to 20%) in a mixture of ethyl acetate/petroleum ether/ triethylamine (50:50:1). Oxalic acid (0.028g) was added to the residue, this was crystallised from ethanol/diethyl ether/ hexane to give 2-((3-amino-1,2,4-oxadiazol-5-yl)methyl) ammonium-1-((3',5'-bis(trifluoromethyl)phenyl)methyloxy)-3,3-diphenylpropane bis oxalate salt mp 135°–136° C., m/e (CI$^+$)=551 (M+H). Found: C, 51.21; H, 4.19; N, 7.61. C$_{27}$H$_{24}$F$_6$N$_4$O$_2$. (C$_2$H$_2$O$_4$)$_2$ requires C, 50.97; H, 3.86; N, 7.66%. $^1$H NMR (360MHz, CDCl$_3$) d 7.99 (1H, s), 7.94 (2H, s), 7.41-7.09 (10H, m), 6.16 (2H, bs), 4.57 (1H, d, J=13.0Hz), 4.48 (1H, d, J=13.0Hz), 4.06 (1H, d, J=10.4Hz), 3.85 (2H, bm), 3.50 (1H, dd, J=10.1Hz, 2.1Hz), 3.30 (1H, dd, J=10.1Hz, 4.8Hz).

EXAMPLE 2

(2S)-2-((3-amino-1,2,4-oxadiazol-5-yl)methyl amino)-1-((3',5'-bis(trifluoromethyl)phenyl)methyloxy)-2-phenylethane a) L-2-Phenylglycinol (5g) and di-t-butyldicarbonate (9.4g) was stirred in a dichloromethane solution (30ml) at room temperature for 3 hours. The precipitate which formed was filtered to give N-t-butoxycarbonyl-L-2-phenylglycinol, 4g.

b) 2-N-t-Butoxycarbonylamino-L-2-phenylglycinol (Example 2a) was alkylated with 3,5-bis(trifluoromethyl)benzyl bromide and deprotected in an analogous manner to that described in Example 1e and f to give L-2-ammonium-1-(3',5'-bis(trifluoromethyl)phenyl)methyloxy-2-phenylethane oxalate salt. mp 84°–90° C. $^1$H NMR (360MHz, MeOH $d_4$) d 7.97 (2H, s), 7.89 (1H, s), 7.47-7.41 (5H, m), 4.8 (2H, AB Jgem= 12.7Hz), 4.61 (1H, t, J=5.93Hz), 3.9 (2H, d, J=5.27Hz). m/e (CI$^+$)=364. Found: C, 48.46; H, 3.75; N, 2.94. C$_{17}$H$_{15}$F$_6$NO.1.4(C$_2$H$_2$O$_4$) requires C, 48.60; H, 3.67; N, 2.86%.

c) (2S)-2-Amino-1-(3',5'-bis(trifluoromethyl)phenyl) methyloxy-2-phenylethane (Example 2b, liberated from its oxalate salt by extraction into CH$_2$Cl$_2$ from aqueous Na$_2$CO$_3$ solution) was alkylated with methyl bromoacetate in an analogous manner to that described in Example 1g to give (2S)-1-((3',5'-bis(trifluoromethyl)phenyl)methyloxy)-2-((carbomethoxy)methyl)ammonium-2-phenylethane oxalate salt. mp 95°–97° C. Found: C, 49.33; H, 3.82; N, 2.61. C$_{20}$H$_{19}$F$_6$NO$_3$.(C$_2$H$_2$O$_4$)$_{1.2}$ requires C, 49.51; H, 3.97; N, 2.58%.

d) Sodium (0.35g) was added to a solution of powdered molecular sieves (A4, 1g) in methanol (17ml) under an atmosphere of nitrogen. To this solution was added hydroxyguanidine hemisulfate hemihydrate (1.2g) and a solution of (2S)-1-((3',5'-bis(trifluoromethyl)phenyl)methyloxy)-2

-(((carbomethoxy)methyl)amino)-2-phenylethane (Example 2e, 1.0g), liberated from its oxalate salt by extraction into $CH_2Cl_2$ from aqueous $Na_2CO_3$ in methanol (2ml) and the solution was heated to reflux for 6 hours. The solution was cooled to ambient temperature, filtered and evaporated to dryness. A solution of the residue in $CH_2Cl_2$ was washed with water, saturated brine and dried ($MgSO_4$). After evaporation the residue was chromatographed on silica gel in ethyl acetate/petroleum ether bp=60°–80° C. (30:70) to give (2S)-((3-amino- 1,2,4-oxadiazol-5-yl)methylamino)-1-((3',5'-bis-(trifluoro methyl)phenyl)methyloxy)-2-phenylethane as an oil. Found: C, 52.0; H, 4.3; N, 11.4. $C_{20}H_{18}N_4O_2F_6 \cdot 0.3(CH_3COC_2H_5)$ requires C, 52.31; H, 4.22; N, 11.51%. m/e $(CI^+)$=461 (M+H). $^1H$ NMR (360MHz, $CDCl_3$) d 7.6 (3H, s, 2,46-($CF_3$)aryl CH), 7.4–7.26 (5H, m, phenyl), 4.6 (2H, s), 4.4 (2H, bs), 4.1 (1H, t, J=5.2Hz), 3.85 (1H, d, J=16.4Hz), 3.72 (1H, d, J=16.4Hz), 3.6 (2H, m), 2.66 (1H, bvs).

EXAMPLE 3

3-[N(-2-((3,5-Bis(trifluormethyl)phenyl) methyloxy)-1-phenylethyl)aminomethyl]-1,2,4-triazole 2(S)-2-Amino-1-(3,5-bis(trifluoromethyl)phenyl)methyloxy-2-phenylethane (2.0g; Example 2b, liberated from its oxalate salt by extraction into $CH_2Cl_2$ from aqueous $Na_2CO_3$ solution) anhydrous potassium carbonate (3.4g) and N-formyl-2-chloroacetamidohydrazone (1.7g) (prepared according to Yanagisawa, I., *J. Med. Chem.*, 1984, 27, 849) were heated to 60° C. in anhydrous dimethylformamide for 3 hours, followed by heating at 130° C. for 12h. The reaction mixture was cooled, diluted with ethyl acetate and washed with water (×3). The ethyl acetate layer was dried ($MgSO_4$), filtered and evaporated to give a brown oil. This was purified on silica eluting with ethyl acetate to afford the title compound as a yellow oil. $^1H$ NMR (360MHz, $CDCl_3$) d 3.64–3.73 (2H, m, $CH_2$), 3.90 (2H, s, $NCH_2$ triazole), 4.04–4.09 (1H, m, NCHPh), 4.63 (2H, s, $OCH_2Ph$), 7.28–7.39 (5H, m, phenyl H), 7.75 (2H, s, ArH), 7.79 (1H, s, ArH), 7.99 (1H, s, triazole-H). m/z $(CI^+)$=445 (M+H). Found: C, 53.49; H, 4.15; N, 12.25. $C_{20}H_{18}F_6N_4O \cdot 0.2 H_2O$ requires C, 53.62; H, 4.14; N, 12.51%.

EXAMPLE 4

1-((3,5-Bis(trifluoromethyl)phenyl)methyloxy)- 3,3-diphenyl-2-(N-(1,2,4-triazol-3-yl)methyl-N-methylamino) propane a) To a solution of 2-t-butoxycarbonylamino-1-((3,5-bis-(trifluoromethyl)phenyl)methyloxy)- 3,3-diphenylpropane (Example 1e, 10.75g) in dimethylformamide (40ml) was added sodium hydride (0.58g, 80% suspension in oil). After stirring the solution at room temperature for 0.5h methyl iodide (1.6ml) was added and the solution stirred for a further 16h. Ethyl acetate (200ml) and water (200ml) were added and the organic phase washed with saturated brine, dried ($MgSO_4$) and evaporated in vacuo. The residue was purified by chromatography on silica gel to give 2-N-t-butoxycarbonyl-N-methylamino-1-((3,5-bis (trifluoromethyl)phenyl)methyloxy)-3,3-diphenylpropane as an oil.

b) The product of Example 4a (2.81g) was dissolved in trifluoroacetic acid (15ml) for 20 minutes. The solvent was removed in vacuo and the residue partitioned between $CH_2Cl_2$ and 2M-NaOH. The organic phase was washed further with 2M-NaOH, saturated brine and dried ($MgSO_4$) to give to give 1-((3,5-bis(trifluoromethyl)phenyl)methyloxy)-2-methylamino- 3,3-diphenylpropane as an oil.

c) The product from Example 4b (1.7g) was dissolved in DMF under a nitrogen atmosphere and potassium carbonate (1.33g) and 2-chloroacetamidhydrazone (0.875g; prepared according to Yanagisawa, I., et al., *J. Med. Chem.*, 1984, 849) were added. The reaction was then heated to 60° C. for 24hr followed by heating to 120° C. for 4hr. After cooling to room temperature ethyl acetate (100ml) and water (20ml) were added. The water layer was then removed and the organic layer washed with water (3×20ml). The organic fraction was dried ($MgSO_4$), filtered and the solvent removed in vacuo. The residue was chromatographed on silica eluting with 50% ethyl acetate/petroleum ether. Removal of solvents in vacuo gave a white solid that was filtered and washed with hexane to give 1-((3,5-bis (trifluoromethyl)phenyl)methyloxy)-3,3-diphenyl-2-(N-(1,2,4-triazol- 3-yl)methyl-N-methyl)aminopropane as a white solid. m.p. 138°–139° C., $^1H$ NMR ($CDCl_3$) d 7.80 (1H, s, triazole (CH=NH), 7.76 (1H, s, ArH), 7.71 (1H, s, ArH), 7.17–7.39 (10H, s, ArH), 4.52 (1H, d, OCHHAr), 4.43 (1H, d, OCHHAr), 4.14 (1H, d, J=14Hz, MeN-CHH-triazole), 4.11 (1H, d, J=11Hz, PhCHPh), 3.88 (1H, d, J=14Hz, MeN-CHH-triazole), 3.78 (1H, brs, MeN-CH-$CH_2O$), 3.66 (1H, d, J=7Hz, $CHHOCH_2Ar$), 3.53 (1H, dd, J=10, 7Hz, $CHHOCH_2Ar$). m/e (ACE) 548 (M$^+$+1). Found: C, 61.70; H, 4.95; N, 10.31. $C_{28}H_{26}N_4OF_6$ requires C, 61.31; H, 4.78; N, 10.21%.

EXAMPLE 5

1-((3,5-Bis(trifluoromethyl)phenyl)methyloxy)-2-{N-((3-thioxo-1,2,4-triazol-5-yl)methyl)-N-methylamino}-3,3-diphenylpropane a) To a solution of the product of Example 1e (0.92g) in N,N-dimethylformamide (10ml) was added sodium hydride (0.08g, 60% suspension in oil) and methyl iodide (0.12ml). After the solution had been stirred at room temperature for 19h water was carefully added and the product was extracted into ethyl acetate. The organic phase was washed with water (twice), saturated brine, dried ($MgSO_4$) and concentrated in vacuo to give 1-((3,5-bis(trifluoromethyl)phenyl)methyloxy)-2-(N-t-butoxy carbonyl(N-methyl)amino)-3,3-diphenylpropane.

b) The product of Example 5a (0.99g) was dissolved in trifluoroacetic add (10ml) and after 0.5h the mixture was concentrated in vacuo. To a solution of the residue dissolved in N,N-dimethylformamide (10ml) was added methyl bromoacetate (0.20ml) and potassium carbonate (0.72g) and the reaction mixture was stirred at 70° C. for 15h. Ethyl acetate and water were added and the organic phase was washed with water (twice), dried ($MgSO_4$) and concentrated in vacuo. The residue was purified by chromatography on silica (eluting with 30% diethyl ether in petroleum ether (bp 60°–80° C.)) to give 1-((3,5-bis(trifluoromethyl)phenyl)methyloxy)-2-((carbomethoxy) methyl-(N-methyl)amino-3,3-diphenylpropane.

c) Hydrazine hydrate (0.18ml) was added to a solution of the product of Example 5b (0.41g) in ethanol (15ml). After heating the solution at reflux for 18h, the solvent was removed in vacuo and the residue partitioned between ethyl acetate and water. The organic phase was dried ($MgSO_4$) and concentrated to give 1-((3,5-bis(trifluoromethyl)phenyl)methyloxy)-2-{ ((formylhydrazino)methyl)-N-methylamino-3,3-diphenyl propane, m/z ($CI^+$) 540 (M+H).

d) 1-((3,5-Bis(trifluoromethyl)phenyl)methyloxy)-2-{((formylhydrazino)methyl)-N-methylamino}-3,3-diphenyl propane (0.37g, Example 5c), potassium thiocyanate (0.13g)

concentrated hydrochloric acid (2ml) and water (10ml) were heated at reflux for 2.75h. After cooling solid potassium hydroxide was added until pH>10 and the solution was extracted twice with ethyl acetate. The combined organics were dried (MgSO$_4$) and the solvent evaporated in vacuo to give 1-((3,5-bis(trifluoromethyl)phenyl)methyloxy)-2-{N-((thiosemi carbazido)methyl)-N-methylamino}-3,3-diphenylpropane, m/z (CI$^+$)=599 (M+H).

This oil was refluxed in 2N NaOH (10ml) for 1.75h. To the cooled reaction mixture was added hydrochloric acid until pH= 4–5 and product partitioned between ethyl acetate and water. The organic phase was dried (MgSO$_4$) and the solvent removed in vacuo. The residue was purified by chromatography on silica (eluting with 40% ethyl acetate in petroleum ether bp 60°–80° C.) to afford 1-((3,5-bis(trifluoromethyl)phenyl)methyloxy)-2-{N-((3-thioxo- 1,2,4-triazol-5-yl)methyl)-N-methylamino}-3,3-diphenylpropane as a white crystalline solid. m.p.=192°–194° C. Found: C, 57.62; H, 4.61; N, 9.67. C$_{28}$H$_{26}$N$_4$OSF$_6$ requires C, 57.92; H, 4.51; N, 9.65%. m/z (CI$^+$)=581 (M+H).

EXAMPLE 6

5-[(N-(2-((3,5-Bis(trifluoromethyl)phenyl) methyloxy)-1-phenylethyl)-N-methylamino)methyl]-2,3-dihydro- 4H-1,2,4-triazol-3-one oxalate salt a) To a solution of 2-N-t-butoxycarbonylamino-L- 2-phenylglycinol (23.7g; Example 2a) and 3,5-bis(trifluoromethyl)benzyl bromide (33.8g) dissolved in dimethylformamide (75ml) was added sodium hydride (80% suspension in oil, 3.3g) in portions over 30 minutes. After stirring the solution at ambient temperature for 1h, water (500ml) and ethyl acetate (500ml) were added. The organic phase was washed further with water (2×100ml), saturated brine and dried (MgSO$_4$). After evaporation in vacuo the residue was chromatographed on silica (eluting with 5% ethyl acetate in petroleum ether bp 60°–80° C.) to give (S)-1-((3,5 bis(trifluoromethyl)phenyl)methyloxy)-2-N-t-butoxycarbonyl amino-2-phenylethane, m.p.=53°–54° C.

b) To a solution of (S)-1-((3,5-bis(trifluoromethyl) phenyl) methyloxy)-2-N-t-butoxycarbonylamino-2-phenylethane (3g; Example 6a) in tetrahydrofuran (10ml) and dimethylformamide (2ml) was added sodium hydride (0.21g; 80% suspension in oil). After the effervescence had subsided (15 minutes) methyl iodide (1.62ml) was added. After stirring the solution for 2h at ambient temperature, water (50ml) and ethyl acetate (50ml) were added and the organic phase was washed with saturated brine and dried (MgSO$_4$). After evaporation to dryness in vacuo the residue was chromatographed on silica (eluting with 0 to 5% ethyl acetate in petroleum ether bp 60°–80° C.) to give (S)-1-((3, 5-bis(trifluoromethyl)phenyl)methyloxy)-2-(N-t-butoxycarbonyl-N-methyl)amino- 2-phenylethane, mp=61° C., m/z (CI$^+$)=478 (M+H).

c) The product of Example 6b (5.26g) was dissolved in methanol saturated with hydrogen chloride (30ml) for 4.5h. The solution was evaporated to dryness and the residue crystallized from diethylether:hexane (1:1) to give 1-((3,5-bis(trifluoromethyl)phenyl)methyloxy)-2-methylamino-2-phenylethane hydrochloride, mp=169°–172° C.

d) Sodium methoxide (0.032g) was added to a solution of chloracetonitrile (1.26ml) in anhydrous methanol (15ml) at 0° C. The reaction mixture was stirred at room temperature for 0.5h and then neutralised with acetic acid (0.034ml). Methyl hydrazinocarboxylate (1.79g) was added and the reaction mixture stirred at room temperature for 0.5h. The solution was concentrated in vacuo to give N-carbomethoxy-2 -chloroacetamidrazone as an orange solid. m/z (CI)$^+$=166 (M+H).

e) The product of Example 6c (liberated as free base by partitioning between ethyl acetate and aqueous Na$_2$CO$_3$ followed by drying (MgSO$_4$) and evaporation; 5.5g), anhydrous K$_2$CO$_3$ and N-carbomethoxy-2-chloroacetamidrazone (3.6g, Example 6d) were heated in anhydrous dimethylformamide at 60° C. for 1h and at 120° C. for 6h. Water (300ml) and ethyl acetate (300ml) were added and the organic phase was washed with water (3×100ml), saturated brine (1×100ml) and dried (MgSO$_4$). After evaporation in vacuo the residue was dissolved in toluene and the solution heated at 120° C. for 6h and at 140° C. for 16h. The solvent was removed in vacuo and the residue chromatographed on silica (eluting with 10% methanol in ethyl acetate). The purified product was dissolved in methanol/ethyl acetate and oxalic acid (1.31g) added. The solution was evaporated to dryness and the residue recrystallized from 5% methanol in ethyl acetate to give 5-((N-((2-((3,5-Bis(trifluoromethyl) phenyl)methyloxy)-1-phenyl)ethyl)-N-methyl)ammonium) methyl]-2,3-dihydro-4H-1,2,4-triazol-3-one oxalate salt. $^1$H NMR (360MHz, MeOD) d 2.44 (3H; s; N-CH$_3$), 3.68 (1H; d; J=14.6; CH$_A$H$_B$CHPh), 3.77 (1H; d; J=14.6Hz; CH$_A$H$_B$CHPh), 3.91–4.06 (2H; m; CH$_2$ triazalone), 4.23 (1H; t; NCHPh), 4.65–4.67 (2H; m; CH$_2$CHPh), 7.30–7.39 (5H; m; Ar H), 7.78–7.79 (3H; m; Ar H). m/z=475 (CI$^+$). Found: C, 48.94; H, 3.93; N, 9.93. C$_{21}$H$_{20}$F$_6$N$_4$O$_2$.C$_2$H$_2$O$_4$ requires C, 49.11; H, 3.76; N, 9.80%.

EXAMPLE 7

5-[(N-((2-((3,5-Bis(trifluormethyl)phenyl) methyloxy)-1-phenylethyl)ammonium)methyl-2,3-dihydro-4H-1,2,4-triazol-3-one oxalate salt The product of Example 2b (2.0g), anhydrous K$_2$CO$_3$ (2.3g) and N-carbomethoxy-2-chloroacetamidrazone (1.3g, Example 6d) were heated at 60° C. in anhydrous dimethyl formamide for 1h, then at 140° C. for 1h. The solution was cooled, dissolved in ethyl acetate (250ml) and water (250ml) and the organic phase washed further with water (×2), saturated brine and dried (MgSO$_4$). The solvent was removed in vacuo and the residue chromatographed on silica (eluting with ethyl acetate) and crystallized as the oxalate salt to give the title compound. $^1$H NMR (360MHz, MeOD) d 3.67 (2H; s; NCH$_2$triazalone), 3.71–3.82 (2H; m; CH$_2$), 4.27–4.30 (1H; m; NCHPh), 4.60–4.67 (2H; m; OCH$_2$Ph), 7.26–7.37 (5H; m; Ar H), 7.78 (1H; s; Ar H), 7.82 (2H; s; Ar H); m/z (CI$^+$)=461 (M+H). Found: C, 49.17; H, 3.66; N, 10.79. C$_{20}$H$_{18}$F$_6$N$_4$O$_2$. 0.7C$_2$H$_2$O$_4$ requires C, 49.11; H, 3.74; N, 10.71%.

EXAMPLE 8

5-[(N-(2-((((3-t-Butyl, 5-methyl)phenyl) methyloxy)-1-phenylethyl))-N-methylamino)methyl]-2,3-dihydro- 4H-1,2,4-triazol-3-one a) 5-tert-butyl-m-xylene (15g) was dissolved in carbon tetrachloride (80ml), N-bromosuccinimide (16.45g) and a catalytic amount of azoisobutyronitrile were added and the reaction was heated at reflux for 4h. The reaction was cooled and the mixture filtered to remove the succinimide. The solvent was removed in vacuo to afford a light brown oil. Purification was carried out by chromatography on silica gel (eluting silica with 100% petroleum ether, bp 60°–800° C.) to afford 3-t-butyl-5-methylbenzyl bromide as a clear oil (15.3g). $^1$H NMR (360MHz, CDCl$_3$) d 1.31 (9H; s; t-Bu), 2.34 (3H; s; CH₃), 4.47 (2H; s; CH₂ Br), 7.04 (1H; s; Ar H), 7.13 (1H; s; Ar H), 7.25 (1H; s; Ar H). m/z (CI⁺)=258 (M+NH₄⁺).

b) (S) 1-(((3-t-butyl-5-methyl)phenyl)methyloxy)-2-methylamino- 2-phenylethane hydrochloride The title compound was prepared by a procedure analogous to that described in Example 6 using (3-t-butyl-5-methyl)benzyl bromide (Example 8a) mp 144°–148° C. $^1$H NMR (360MHz, DMSO) d 1.24 (9H; s; tert-Bu), 2.27 (3H; s; Ar CH₃), 2.39 (3H; s; N-CH₃), 3.78–3.83 (1H; dd; $J_{AB}$=11Hz, J=5Hz; CH-CHH0), 3.89–3.94 (1H, dd, $J_1$=11Hz $J_2$=7Hz, CHCHHO), 4.46–4.56 (3H, m, OCH₂+CHPh), 6.92 (1H, s, ArH), 7.09 (1H, s, ArH), 7.11 (1H, s, ArH), 7.43–7.47 (3H, m, ArH), 7.56–7.61 (3H, m, ArH).

c) The product of Example 8b was converted to the title compound by reaction with N-carbomethoxy- 2-chloroacetamidrazone (Example 6a) in an analogous manner to that described in Example 6e to give 5-[(N-(2-((((3-t-Butyl, 5-methyl)phenyl)methyloxy)-1-phenylethyl))-N-methylamino) methyl]-2,3-dihydro-4H-1,2,4-triazol-3-one. Mp 125°–130° C. $^1$H NMR (360MHz, DMSO) d 1.27 (9H; s; t-Bu), 2.28 (3H; s; Ar CH₃), 2.59 (3H; bs; N-CH₃), 3.92–3.99 (3H; m), 4.15–4.22 (1H; m), 4.51–4.61 (3H; m), 6.89 (1H; s; Ar H), 7.06 (1H; s; Ar H), 7.11 (1H; s; Ar H), 7.34–7.45 (3H; m; Ar H), 7.58–7.60 (2H; m; Ar H). m/z (CI⁺)=409 (M+H⁺, 100%). Found: C, 62.47; H, 7.67; N, 12.49. C₂₄H₃₂N₄O₂.HCl requires C, 62.26; H, 7.62; N, 12.15.

EXAMPLE 9

5-[((N-(1-((3,5-Bis(trifluoromethyl)phenyl) methyloxy)-3,3-diphenylprop-2-yl)-N-methyl)amino)methyl]-2,3-dihydro- 4H-1,2,4-triazol-3-one 1-((3,5-Bis(trifluormethyl)phenyl)methyloxy)-2-methylamino- 3,3-diphenylpropane (Example 4b, 1.15g), N-Carbomethoxy- 2-chloroacetamidrazone (Example 6d, 0.49g) and potassium carbonate (1.02g) were heated in dimethylformamide (30ml) at 60° C. for 20min. The reaction mixture was then heated to 160° C. for 1.5h before cooling, diluting with water and extracting the product into ethyl acetate. The organic phase was washed with water (30ml) and brine (30ml) dried (MgSO₄) and evaporated to dryness. The product was purified on silica eluting with petroleum ether/ethyl acetate mixtures to give the title compound. $^1$H NMR (360MHz, DMSO-d₆) d 3.26–3.30 (1H, m), 3.48–3.51 (3H, m), 3.60–3.80 (1H, m), 4.06 (1H, d, J=10.3Hz), 4.47–4.58 (2H, ABq, J=13.1Hz), 7.08–7.35 (10H, m), 7.94 (2H, s) and 8.0 (1H, s). Found: C, 59.57; H, 4.64; N, 9.93; C₂₈H₂₆N₄O₂F₆ requires C, 59.59; H, 4.57; N, 9.97%.

EXAMPLE 10

5-[(N-(1-((3,5-Bis(trifluoromethyl)phenyl) methyloxy)-3,3-diphenylprop-2-yl)amino)methyl]-2,3-dihydro-4H- 1,2,4-triazol-3-one The title compound was prepared from 2-amino-1-((3,5-bis (trifluoromethyl)phenyl)methyloxy)-3,3-diphenylpropane (Example 1f) using a procedure analogous to that described in Example 9. $^1$H NMR (360MHz, DMSO-d₆) δ 3.28 (1H, q, J=4.4 and 10Hz), 3.48–3.51 (3H, m), 3.70–3.76 (1H, m), 4.06 (1H, d, J= 9.6Hz), 4.47–4.57 (2H, ABq, J=13Hz), 7.08–7.35 (10H, m), 7.94 (2H, s) and 8.0 (1H, s). Found: C, 54.73; H, 4.11; N, 8.85; C₂₇H₂₄N₄O₂F₆. C₂H₂O₄ requires C, 54.38; H, 4.09; N, 8.75%.

EXAMPLE 11

5-[(N-((2S)-2-(1-(3,5-dichlorophenyl) methyloxy)-2-phenyl)ethyl)aminomethyl]-2,3-dihydro-4H-1,2,4-triazol-3-one The title compound was prepared using a procedure analogous to that described in Example 8b, mp 124°–127° C. $^1$H NMR (360MHz, MeOD) δ 2.45 (3H, s, N-CH₃), 3.71 (1H, d, J=14.59Hz, CH$_A$H$_B$CHPh), 3.78 (1H, d, J=14.59Hz, CH$_A$H$_B$CHPh), 3.84–4.00 (2H, m), 4.23 (1H, t, NCHPh), 4.47 (2H, m, CH₂Ar), 7.17 (2H, s, ArH), 7.32 (1H, s, ArH), 7.34–7.36 (5H, m ArH) m/z (CI⁺)=408. Found: C, 50.38; H, 4.52; N, 11.09. C₁₉H₂₀Cl₂N₄O₂·C₂H₂O₄ requires C, 50.72; H, 4.46; N, 11.27%.

EXAMPLE 12

(S)-5-[N-(1-(2-((3,5-Bis(trifluoromethyl)phenyl) methyloxy)-1-phenyl)ethyl)aminomethyl]imidazolidine-2,4-dione hydrochloride a) (S)-2-((3,5-Bis(trifluoromethyl)phenyl)methyloxy)-1-phenyl- 1-(N-t-butoxycarbonylamino)ethane (1.1g, Example 2b) was dissolved in 20ml anhydrous DMF and sodium hydride (0.085g) was added. The reaction mixture was stirred for 20 min and allyl bromide (0.300g) added and stirred for a further 16h. The reaction was quenched by the addition of water (30ml) and poured into 100ml ethyl acetate. The organic layer was washed with water (3×20ml), brine and dried (MgSO₄). The solvent was removed in vacuo and the residue chromatographed on silica eluting with 10% Ethyl acetate/hexane to give (S)-2-((3,5 -bis(trifluoromethyl)phenyl)methyloxy)-1-phenyl-1 -(N-t-butoxycarbonyl-N-allylamino)ethane as a colourless oil 0.980g. m/z=504 (M+H).

b) The product of Example 12a (4.00g) was dissolved in 1:1 MeOH/CH₂Cl₂ (10ml) and cooled to −78° C. Ozone was bubbled through the reaction mixture for 0.5h. N₂ was then bubbled through for 5 min and methyl sulfide (0.17ml) was added. After warming the reaction mixture to room temperature, the solvent was removed to give the crude aldehyde, m/z=506 (M+H). The crude aldehyde (0.390g) was dissolved in 1:1 ethanol/water (10ml) and potassium cyanide (0.100g) was added followed by ammonium carbonate (0.370g) and the reaction stirred at 65° C. for 16h. The ethanol was then removed and the aqueous layer extracted with ethyl acetate (2×50ml). The organic layers were combined, washed with satd. NH₄Cl and dried (MgSO₄) filtered and the solvent removed in vacuo. The resulting residue was chromatographed on silica eluting with 40% ethyl acetate/hexane to give a colourless oil, m/z=576 (M+H). This intermediate was then dissolved in anhydrous HCl/MeOH and stirred for 2h. The solvent was then removed and the compound precipitated with ether to give 5-[N-(1-(2-((3,5 -bis(trifluoromethyl)phenyl)methyloxy)-1-phenyl)ethyl) aminomethyl]imidazolidine-2,4-dione hydrochloride as a white solid. $^1$H NMR (CDCl₃) δ 7.81 (4H, m, Ar-H and CONHCO), 7.3 (5H, m, Ar-H), 6.5 (1H, s, C-CH-NH), 4.6 (1H, dd, CH-Ph), 3.8–4.2 (2H, m, OCH₂Ar), 3.5 (2H, m, CH₂O), 2.8–3.0 (2H, m, NH-CH₂-Het). m/z=476 (M+H). Anal. Calcd. for C₂₁H₂₀N₃O₃F₆Cl: C, 49.27; H, 3.94; N, 8.20: Found: C, 49.60; H, 3.94; N, 8.50%.

EXAMPLE 13

(S)-3-[N-(1-(2-((3,5-Bis(trifluoromethyl) phenyl)methyloxy)-1-phenyl)ethyl)-N-methylaminomethyl]-1,2,4-triazole The title compound was prepared as an oil from (S)-1-((3,5-bis(trifluoromethyl)phenyl)methyloxy)-2-(N-t-butoxycarbonyl-N-methyl)amino- 2-phenylethane (Example 6b) using a procedure analogous to that described in Example 4c. $^1$H NMR (360MHz, CDCl$_3$) δ 2.33 (3H, s), 3.67–3.72 (1H, m), 3.80–3.84 (1H, dd), 3.75– 4.06 (4H, m), 4.66 (2H, s), 7.31–7.40 (5H, m), 7.72 (2H, s), 7.79 (1H, s), 8.00 (1H, s). m/z (CI$^+$)=459. Found: C, 54.91; H, 4.49; N, 11.87. C$_{21}$H$_{20}$F$_6$N$_4$O requires C, 55.02; H, 4.40; N, 12.22%.

EXAMPLE 14

(S)-5-[N-(1-(2-((3,5-Bis(trifluoromethyl) phenyl)methyloxy)-1-phenyl)ethyl)-N-ethylaminomethyl]-2,3-dihydro-4H-1,2,4-triazol-3-one The title compound was prepared as an oil by a procedure analogous to that described in Example 6 using ethyl iodide. $^1$H NMR (DMSO-d$_6$) δ 0.93 (3H, t), 2.40–2.45 (1H, m), 2.55–2.65 (1H, m), 3.38 (1H, d, J=14.93Hz), 3.55 (1H, d, J=14.93Hz), 3.88–4.05 (3H, m), 4.66 (2H, dd), 7.22–7.33 (3H, m), 7.40 (1H, s), 7.41 (1H, s), 7.84 (2H, s), 7.89 (1H, s), 10.90 (2H, bs). m/z (CI$^+$)=489 (M+H). Found: C, 54.47; H, 4.59; N, 11.26. C$_{22}$H$_{22}$F$_6$N$_4$O$_2$ requires C, 54.10; H, 4.54; N, 11.47%.

EXAMPLE 15

(S)-5-[N-(1-(2-((3,5-Bis(trifluoromethyl) phenyl)methyloxy)-1-phenyl)ethyl)-N-propylaminomethyl]-2,3-dihydro-4H-1,2,4-triazol-3-one The title compound was prepared as an oil by a procedure analogous to that described in Example 6 using propyl iodide. $^1$H NMR (360MHz, DMSO-d$_6$) δ 0.72 (3H, t), 1.33–1.39 (2H, m), 2.22– 2.30 (1H, m), 2.38–2.43 (1H, m), 3.26 (1H, d, J=14.73Hz), 3.57 (1H, d, J=14.73Hz), 3.94–4.04 (3H, m), 4.67 (2H, dd), 7.24–7.41 (5H, m), 7.87 (2H, s), 7.98 (1H, s), 11.16 (1H, s), 11.23 (1H, bs). m/z (CI$^+$)=503. Found: C, 54.62; H, 4.68; N, 10.94. C$_{23}$H$_{24}$F$_6$N$_4$O$_2$ requires C, 54.98; H, 4.82; N, 11.15%.

EXAMPLE 16

(R)-5-[N-(1-(2-((Bis(trifluoromethyl) phenyl)methyloxy)-1-phenyl)ethyl)-N-ethylaminomethyl)-2,3-dihydro-4H- 1,2,4-triazol-3-one The title compound was prepared using a procedure analogous to that described in Example 6 starting with D-phenylglycinol, mp 165°–169° C. $^1$H NMR (360MHz, MeOD) δ 1.2 (3H, t), 2.86–2.95 (1H, m), 3.05–3.14 (1H, m), 3.86 (1H, d, J= 15.19Hz), 4.04–4.16 (3H, m), 4.52 (1H, t), 4.73 (2H, dd), 7.37–7.44 (3H, m), 7.49–7.52 (2H, m), 7.87 (3H, s). m/z (CI$^+$)=489. Found: C, 50.05; H, 4.02; N, 9.83. C$_{22}$H$_{22}$F$_6$N$_4$O$_2$·C$_2$H$_2$O$_4$ requires C, 49.83; H, 4.18; N, 9.69%.

EXAMPLE 17

(S)-3-[1-{N-(1-(2-((3,5-bis(trifluoromethyl) phenyl)methyloxy)-1-phenyl)ethyl)-N-ethylamino}ethyl]1,2,4-triazole a) Sodium methoxide (0.162g) was added to a solution of 2-chloropropionitrile (10.5g) in anhydrous methanol (150ml) at 0° C. The reaction mixture was stirred at room temperature for 1h, then neutralised with acetic acid (0.18ml). N-Formylhydrazine (7.04g) was added and the mixture was stirred overnight. The resulting pink solution was concentrated in vacuo to give N-formyl-2-chloropropionamidohydrazone as a pink solid.

b) The title compound as a mixture of diastereomers (1:1) was prepared as an oil by a procedure analogous to that described in Example 3 using N-formyl-2-chloropropionamidohydrazone (Example 17a). $^1$H NMR (360MHz, CDCl$_3$) δ 1.00 (1.5H, t, J= 7.10Hz), 1.08 (1.5H, t, J=7.10Hz), 1.24 (1.5H, d, J=9.03Hz), 1.54 (1.5H, d, J=7.00Hz), 2.63–2.92 (2H, m), 3.66–4.06 (2H, m, 4.21–4.36 (2H, m), 4.70–4.71 (2H, m), 7.26–7.39 (5H, m), 7.73–7.89 (3H, m). m/z (CI$^+$)=487. Found: C, 56.64; H, 4.87; N, 10.82. C$_{23}$H$_{24}$F$_6$N$_4$O·0.2C$_4$H$_8$O$_2$ requires C, 56.71; H, 5.12; N, 11.12%.

EXAMPLE 18

(S)-5-[N-(1-(2-((3,5-Bis(trifluoromethyl) phenyl)methyloxy)-1-phenyl)ethyl)aminomethyl]-tetrazole a) Bromoacetonitrile (570 μl) was stirred in a 0.5M solution of anhydrous DMF (15ml) at 60° C. with potassium carbonate (2.07g) for 5 minutes before (S)-2-amino-1-((3, 5-bis(trifluoromethyl) phenyl)methyloxy)-2-phenylethane (2.7g, Example 2b, liberated from the salt by extraction into ethyl acetate from aqueous Na$_2$CO$_3$ solution) was added. After 1.5 hours, the solution was cooled and the reaction quenched with water (100ml) and diluted with Ethyl acetate (60ml). The mixture was separated and the aqueous layer further extracted with ethyl acetate (4×30ml). The combined organic extracts were washed with brine (1×30ml), dried (MgSO$_4$) and evaporated to a dark oil (4.1g). The crude oil was purified by flash silica gel chromatography in Ethyl acetate/hexane (1:1) to yield (S)-1-((3,5 -bis(trifluoromethyl)phenyl)methyloxy)-2-cyanomethylamino-2-phenylethane as a viscous oil 2.5g. $^1$H NMR (250MHz, CDCl$_3$) δ 7.82 (1H, s, Ar), 7.79 (2H, s, ArH), 7.36 (5H, m, Ph), 4.67 (2H, s, OCH$_2$Ar), 4.27 (1H, t, J=6.5Hz, PhCHN), 3.68 (1H, d, J=17Hz) and 3.31 (1H, d, J=17Hz, CH$_2$CN). m/z (CI$^+$) 403 (M+1, 100%).

b) (S)-1-((3,5-Bis(trifluoromethyl)phenyl)methyloxy)-2-cyanomethylamino- 2-phenylethane (2.41g, Example 18a) was heated with triethylamine hydrochloride (1.32g, 9.6mmol) and sodium azide (1.17g) in anhydrous 2-methylpyrrolidinone (12ml) at reflux for 1.5 hours. The cooled solution was poured into ice/water (140ml), acidified to pH 2 with 2N HCl and extracted with Ethyl acetate (5×30ml). The combined organic extracts were washed with brine (1×20ml), dried (MgSO$_4$) and evaporated to dryness (3.5g). The crude residue was purified by flash silica gel chromatography in dichloromethane-methanol (9:1), to give a white solid (1.97g). Crystallisation from Ethyl acetate-hexane yielded (S)-5-[N-(1-(2-((3,5 -bis(trifluoromethyl)phenyl)methyloxy)-1-phenyl)ethyl) aminomethyl]tetrazole as a white powder, mp 81°–82° C. (sinters 68°–75° C). $^1$H NMR (360MHz, DMSO-d$_6$) δ 8.00 (1H, s) and 7.93 (2H, s, ArH), 7.43 (2H, m) and 7.29–7.38 (3H, m, Ph), 4.67 (2H, s, OCH$_2$Ar), 4.10 (1H, bs, PhCHN), 3.69 (2H, s, NCH$_2$CN), 3.62– 3.73 (2H, m, CH$_2$O). m/z (CI$^+$) 446 (M+1, 5%); (CI$^-$) 425 (M-HF, 18%), 242 (ArCHO, 100%). Found: C, 51.23; H, 3.85; N, 15.73. C$_{19}$H$_{17}$F$_6$N$_5$O requires C, 51.25; H, 3.94; N, 15.07%.

EXAMPLE 19

(S)-5-[N-(1-(2-((3,5-Bis(trifluoromethyl) phenyl)methyloxy)-1-phenyl)ethyl)aminomethyl]-2-N-methyl tetrazole (S)-5-[N-((2-((3,5-Bis(trifluoromethyl)phenyl)methyloxy)-1 -phenyl)ethyl)aminomethyl]tetrazole (1.50g, Example 18) was suspended in ice-cold diethyl ether (20ml) and treated with a slight excess of ethereal diazomethane solution. The reaction was allowed to warm to room temperature and after 3 hours, a few drops of glacial acetic acid were added. The solution was evaporated to dryness (1.6g) and the crude concentrate purified by flash silica gel chromatography in Ethyl acetate-hexane (30– 50%) to yield the title compound as clear oil. $^1$H NMR (360MHz, DMSO-$d_6$) δ 7.98 (1H, s) and 7.95 (2H, s, ArH), 7.25–7.41 (5H, m, Ph), 4.68 (2H, s, OCH$_2$Ar), 4.31 (3H, s, NMe), 4.00 (1H, t, J= 6.4Hz, PhCHN), 3.85 (1H, d, J=14.5Hz) and 3.72 (1H, d, J= 14.5Hz, CH$_2$N), 3.55–3.65 (2H, m, CH$_2$O). m/z (CI$^+$)=460 (M+1, 100%). Found: C, 52.20; H, 3.85; N, 15.37. C$_{20}$H$_{19}$F$_6$N$_5$O requires C, 52.28; H, 4.18; N, 15.25%.

EXAMPLE 20

(S)-5-[N-(1-(2-((3,5-Bis(trifluoromethyl) phenyl)methyloxy)-1-phenyl)ethyl)aminomethyl]1-N-methyltetrazole The title compound was prepared as an oil by a procedure analogous to that described in Example 19. $^1$H NMR (360MHz, DMSO-$d_6$) δ 8.03 (1H, s) and 7.97 (2H, s, ArH), 7.30–7.43 (5H, m, Ph), 4.70 (2H, s, OCH$_2$Ar), 4.00 (3H, s, tet-NMe), 3.85–4.02 (3H, bm, CH$_2$NCHPh), 3.59–3.69 (2H, m, CH$_2$O), 3.36 (3H, s, NMe). m/z (CI$^+$)=460 (M+1, 100%).

EXAMPLE 21

(S)-5-[N-(1-(2-((3,5-Bis(trifluoromethyl) phenyl)methoxy)-1-phenyl)ethyl)-N-methyl-aminomethyl]tetrazole oxalate salt a) 1-((3,5-Bis(trifluoromethyl)phenyl)methoxy)-2-methylamino- 2-phenylethane (3.82g, Example 6c) was reacted in an analogous procedure as described in Example 18a to give (S)-1-((3,5-bis(trifluoromethyl)phenyl)methyloxy)-2-(N-methyl-N-(cyanomethyl)amino)- 2-phenylethane as large, pale yellow plates 3.44g. mp 110°–111° C. (MeOH). $^1$H NMR (360MHz, CDCl$_3$) δ 7.77 (1H, s) and 7.68 (2H, s, ArH), 7.37 (5H, m, Ph), 4.62 (1H, d, J= 12.8Hz) and 4.56 (1H, d, J=12.8Hz, OCH$_2$Ar), 3.87 (1H, dd, J= 10.2, 5.7Hz, PhCHN), 3.66–3.78 (3H, m, CH$_2$CN and CHHO), 3.48 (1H, d, J=17.2Hz, CHHO), 2.45 (3H, s, NMe). m/z (CI$^+$)= 417 (M+1, 100%).

b) The title compound was prepared by a procedure analogous to that described in Example 18b. Purification by flash silica gel chromatography yielded the product as a gum (3.3g). The oxalate salt was prepared which yielded a white solid. mp 104°–106° C. (Et$_2$O). $^1$H NMR (360MHz, DMSO-$d_6$, free base) δ 7.97 (1H, s) and 7.87 (2H, s, ArH), 7.28–7.46 (5H, m, Ph), 4.68 (2H, s, OCH$_2$Ar), 3.87–4.02 (5H, m, CH$_2$N(Me)CH(Ph)CH$_2$O), 2.16 (3H, s, NMe). m/z (CI$^+$, free base)=460 (M+1, 100%). Found: C, 48.46; H, 3.75; N, 12.24. C$_{20}$H$_{19}$F$_6$N$_5$O.(COOH)$_2$ requires C, 48.09; H, 3.85; N, 12.75%.

EXAMPLE 22

5-[N-(1-(2-((3,5-Bis(trifluoromethyl) phenyl)methyloxy)-1-phenyl)ethyl)-N-methylaminomethyl]-2-N-methyltetrazole The title compound was prepared by a procedure analogous to that described in Example 21. $^1$H NMR (360MHz, $d_6$-DMSO) δ 7.98 (1H, s) and 7.86 (2H, s, ArH), 7.27–7.41 (5H, m, Ph), 4.67 (2H, s, OCH$_2$Ar), 4.33 (3H, s, tet-NMe), 3.64–4.01 (4H, m, CH$_2$N(Me)CHCHHO), 3.76 (1H, d, J=14.4Hz, CHHO), 2.17 (3H, s, NMe). m/z (CI$^+$) 474 (M+1, 100%). Found: C, 52.82; H, 4.41; N, 15.03. C$_{21}$H$_{21}$F$_6$N$_5$O requires C, 53.28; H, 4.47; N, 14.79%.

EXAMPLE 23

(S)-5-[N-(1-(2-((3,5-Bis(trifluoromethyl) phenyl)methyoxy)-1-phenyl)ethyl-N-methyl-aminomethyl]-1-N-methyl tetrazole The title compound was prepared by a procedure analogous to that described in Example 19. $^1$H NMR (360MHz, DMSO-$d_6$) δ 8.00 (1H, s) and 7.90 (2H, s, ArH), 7.30–7.40 (5H, m, Ph), 4.69 (2H, s, OCH$_2$Ar), 3.61–4.07 (5H, m, CH$_2$N(Me)CH.(Ph).CH$_2$O), 2.07 (3H, s, NMe). m/z (CI$^+$)= 474 (M+1, 100%). Found: C, 53.00; H, 4.40; N, 14.76. C$_{21}$H$_{21}$F$_6$N$_5$O requires C, 53.28; H, 4.47; N, 14.78%.

EXAMPLE 24

(R)-5-[N-(1-(2-((3,5-Bis(trifluoromethyl) phenyl)methyloxy)-1-phenyl)-ethyl)-N-methylaminomethyl]tetrazole a) (R)-1-((3,5-Bis(trifluoromethyl)phenyl)methyloxy)-2-(N-cyanomethyl-N-methylamino)-2-phenylethane was prepared by a procedure analogous to that described in Example 21 from the (R) phenylglycinol, mp=110°–111° C. All spectra data was identical to that described in Example 21a.

b) The title compound isolated as the oxalate salt was prepared by a procedure analogous to that described in Example 21b, mp 108°–109° C. (Et$_2$O) giving identical spectral data.

EXAMPLE 25

(R)-5-[N-(1-(2-((3,5-Bis(trifluoromethyl) phenyl)methyloxy)-1-phenyl)ethyl)-N-methylaminomethyl]-2-N-methyltetrazole The title compound was prepared by a procedure analogous to that described in Example 19. All spectral data was identical to that described in Example 22.

EXAMPLE 26

(R)-5-[N-(1-(2-((3,5-Bis(trifluoromethyl) phenyl)methyloxy)-1-phenyl)ethyl)-N-methylaminomethyl]-1-N-methyltetrazole The title compound was prepared by a procedure analogous to that described in Example 19. All Spectral data was identical to that described in Example 23.

EXAMPLE 27

(S)-5-[2-{N-(1-(2-((3,5-Bis(trifluoromethyl) phenyl)methyloxy)-1-phenyl)ethyl)-N-methylamino}ethyl]-tetrazole Oxalate salt a) 1-((3,5-Bis(trifluoromethyl)phenyl)methyloxy)-2-methylamino- 2-phenyl ethane (1.70g, Example 6c, free base) was heated at reflux with acrylonitrile (329 µl) in anhydrous methanol (10ml) for 18 hours. The solution was evaporated to dryness (2.0g). The crude black oil was purified by flash silica gel chromatography in hexane-Ethyl acetate (4:1) to yield (S)-1-((3,5 -bis(trifluoromethyl)phenyl)methyloxy)-2-(N-methyl-N-2-(cyanoethyl)amino)- 2-phenylethane as a lightly coloured oil, 1.30g. $^1$H NMR (360MHz, DMSO-$d_6$) δ 7.98 (1H, s) and 7.89 (2H, s, ArH), 7.25–7.37 (5H, m, Ph), 4.69 (2H, s, OCH$_2$Ar), 3.81–3.95 (3H, m, PhCH.CH$_2$O), 2.56–2.75 (4H, m, CH$_2$CH$_2$CN), 2.18 (3H, s, NMe). m/z (CI$^+$)=431 (M+1, 100%). Found: C, 58.67; H, 4.72; N, 6.42. C$_{21}$H$_{20}$F$_6$N$_2$O requires C, 58.60; H, 4.68; N, 6.51%.

b) The title compound was prepared from the product of Example 27a by an analogous procedure as described in Example 17b. Purification by flash silica gel chromatography in dichloromethane-methanol (19:1) yielded the product which was crystallised as the oxalate salt, mp 72°–73° C. (Et$_2$O). $^1$H NMR (360MHz, DMSO-d$_6$) δ 7.99 (1H, s) and 7.89 (2H, s, ArH), 7.32 (5H, m, Ph), 4.68 (2H, s, OCH$_2$-Ar), 4.08 (1H, t, J=6.1Hz, PhCH), 3.95 (1H, m) and 3.85 (1H, m, CH$_2$O), 3.10 (2H, t, J= 7Hz) and 2.86–3.01 (2H, m, CH$_2$CH$_2$N), 2.32 (3H, s, NMe). m/z (CI$^+$)=474 (M+1, 100%). Found: C, 49.16; H, 4.02; N, 12.27. C$_{21}$H$_{21}$F$_6$N$_5$O.(COOH)$_2$ requires C, 49.03; H, 4.11; N, 12.43%.

EXAMPLE 28

(S)-5-[N-((2-(((3-Chloro-5-methyl)phenyl) methyloxy)-1-phenyl)ethyl)-N-methylaminomethyl]-2,3-dihydro- 4H-1, 2,4-triazol-3-one The title compound was prepared in an analogous procedure as described in Example 6 using 3-chloro-5-methylbenzyl bromide as the alkylating agent, mp 108°–110° C. m/z (CI$^+$)=386 (M+H). Found: C, 54.71; H, 5.87; N, 12.51. C$_{20}$H$_{23}$N$_4$O$_2$Cl.H$_2$O.HCl requires C, 54.43; H, 5.92; N, 12.69%.

EXAMPLE 29

(S)-5-[N-{1-((3,5-Bis(triflouromethyl) phenyl)methyloxy)-3,3-diphenylprop-2-yl}-N-methylamino methyl]2,3-dihydro-4H-1,2,4-triazol-3-one The title compound was prepared in an analogous procedure as described in Example 1a–f, 4a, b and 9 using (S)-β,β-diphenylalanine hydrochloride. All spectral data was identical to that described in Example 9.

EXAMPLE 30

(R)-5-[N-}1-((3,5-Bis(trifluoromethyl) phenyl)methyloxy)-3,3-diphenylprop-2-yl}-N-methylamino methyl]-2,3-dihydro-4H-1,2,4-triazol-3-one The title compound was prepared in an analogous procedure as described in Example 1a–f, 4a, b and 9 using (R)-β,β-diphenylalanine hydrochloride. All spectral data was identical to that described in Example 9.

EXAMPLE 31

5-[N-}1-((3,5-Bis(trifluoromethyl)phenyl) methyloxy)-3,3-diphenylprop-2-yl}-N-ethylaminomethyl]-2,3-dihydro-4H-1,2,4-triazol-3-one a) 1-((3,5-Bis(trifluoromethyl)phenyl)methyloxy)-2-ethylamine- 3,3-diphenylpropane was prepared in an analogous procedure as outlined in Examples 4a and 6 using ethyl iodide in place of methyl iodide.

b) The title compound was prepared using the product from Example 31a in an analogous procedure as outlined in Example 9. $^1$H NMR (360MHz, DMSO-d$_6$) δ 7.99 (1H, s), 7.89 (2H, s), 7.39- 7.08 (10H, m), 4.49-4.42 (2H, ABq, J=13.1Hz), 4.20 (1H, d, J= 11.5Hz), 4.00-3.96 (1H, m), 3.57-3.46 (4H, m), 2.72-2.54 (2H, m) and 0.73 (3H, t, J=6.9Hz). m/z (CI$^+$)=579 (M+H).

EXAMPLE 32

5-[N-[1-((3,5-Bis(trifluoromethyl)phenyl) methyloxy)-3,3-diphenylprop-2-yl]-N-methyl-aminomethyl]-N-methyl-2,3-dihydro-4H-1,2,4-triazol-3-one To a solution of the product from Example 9 (0.1g) in dimethylformamide (5ml) was added sodium hydride (80% suspension in oil, 0.0065g) and methyl iodide (0.055ml). After stirring the solution at room temperature for 18h water and ethyl acetate were added. The organic phase was washed with water (5×100ml) and brine, dried (MgSO$_4$) and evaporated in vacuo. Purification by chromatography on silica gel (eluting with mixtures of ethyl acetate and petroleum ether bp 60°–80° C.) gave the title compound as an oil. $^1$H NMR (360MHz, CDCl$_3$) δ 7.80 (1H, s), 7.70 (2H, s), 7.32-7.09 (10H, m), 4.43-4.31 (2H, ABq, J= 12.5Hz), 4.10 (1H, d, J=11.3Hz), 3.86-3.51 (5H, m), 3.42 (3H, s), 2.40 (3H, d, J=7.5Hz).

The following examples illustrate pharmaceutical compositions according to the invention.

EXAMPLE 33A Tablets containing 1–25mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 33B Tablets containing 26–100mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0mg, 2.0mg, 25.0mg, 26.0mg, 50.0mg and 100mg of the active compound per tablet.

EXAMPLE 34 Parenteral injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 35 Topical formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

---

We claim:

1. A compound of formula (I), or a pharmaceutically acceptable salt or prodrug thereof:

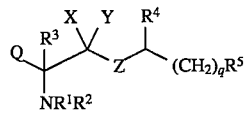

(I)

wherein

Q represents optionally substituted phenyl or optionally substituted benzhydryl; wherein said substituents are selected from the group consisting of: $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$alkyl, phenyl or trifluoromethyl;

X and Y each represent H or X and Y together form a group =O;

Z represents O, S or $NR^8$, where $R^8$ represents H or $C_{1-6}$alkyl;

$R^1$ represents H, $C_{1-6}$alkyl optionally substituted by hydroxy, cyano, $COR^a$, $COOR^a$, $CONR^aR^b$, $COC_{1-4}$alkyl$NR^aR^b$, $CONR^aC_{1-4}$alkyl$CONR^aR^b$ or $NR^aR^b$, (where $R^a$ and $R^b$ each independently represent H, $C_{1-6}$alkyl or phenyl or phenyl$C_1$-$C_4$alkyl optionally substituted in either of the phenyl rings by one or more of $C_{1-6}$alkyl, $C_{1-6}$alkoxy, halo and trifluoromethyl), phenyl($C_{1-4}$alkyl), (optionally substituted by one or more of $C_{1-6}$alkyl, $C_{1-6}$alkoxy, halo and trifluoromethyl in the phenyl ring), $C_{2-6}$alkenyl, $COR^a$, $COOR^a$, $CONHR^a$, $COC_{1-4}$alkyl$NR^aR^b$, or $CONR^aC_{1-4}$ alkyl$CONR^aR^b$ where $R^a$ and $R^b$ are as previously defined;

R² represents C₁₋₄alkyl substituted by an optionally substituted aromatic heterocycle selected from the group consisting of: thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which can be substituted by one or more substituents selected from the group consisting of: $C_{1-6}$alkyl, $C_{1-6}$alkoxy, phenyl, oxo, thioxo, halo, trifluoromethyl, $NR^cR^d$, $NR^cCOR^d$, $CONR^cR^d$, $CO_2R^c$, $SR^c$, $SO_2R^c$ and $CH_2OR^c$, where $R^c$ and $R^d$ are as previously defined;

R³ represents H, $C_{1-6}$alkyl or $C_{2-6}$alkenyl;

R⁴ represents H, $C_{1-6}$alkyl or phenyl (optionally substituted by one or more of $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$alkyl, phenyl or trifluoromethyl);

R⁵ represents phenyl optionally substituted by one or more of $C_{1-6}$alkyl, $C_{2-6}$alkenyl, $C_{2-6}$alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined; and q is 0, 1, 2 or 3.

2. A compound as claimed in claim 1 wherein R² represents C₁₋₄alkyl substituted by an optionally substituted 5- or 6-membered aromatic heterocycle.

3. A compound as claimed in claim 2 wherein R² represents C₁₋₄alkyl substituted by optionally substituted oxadiazolyl, imidazolyl, triazolyl or tetrazolyl.

4. A compound as claimed in claim 1 wherein Q represents optionally substituted phenyl.

5. A compound as claimed in claim 1 wherein Q represents optionally substituted benzhydryl.

6. A compound as claimed in claim 1 wherein R¹ is H or $C_{1-6}$alkyl.

7. A compound as claimed in claim 1 wherein R⁴ is H or $C_{1-6}$alkyl.

8. A compound as claimed in claim 1 wherein q is zero and R⁵ is substituted phenyl.

9. A compound as claimed in claim 1 wherein X and Y each represent H and Z represents O.

10. A compound as claimed in claim 1 selected from:
2-((3-amino-1,2,4-oxadiazol-5-yl)methylammonium)-1-((3',5'-bis(trifluoromethyl)phenyl)methyloxy)-3,3-diphenylpropane;
(2S)-2-((3-amino-1,2,4-oxadiazol-5-yl)methylammonium)-1-((3',5'-bis(trifluoromethyl)phenyl)methyloxy)-2-phenylethane;
3-[N-(2-((3,5-bis(trifluoromethyl)phenyl)methyloxy)-1-phenylethyl)aminomethyl] -1,2,4 -triazole;
1-((3,5-bis(trifluoromethyl)phenyl)methyloxy)-3,3-diphenyl- 2-(N-(1,2,4-triazol-3-yl)methyl-N-methylamino)propane;
1-((3,5-bis(trifluoromethyl)phenyl)methyloxy)-2-[N-((3-thioxo- 1,2,4-triazol-5-yl)methyl)-N-methylamino]-3,3-diphenylpropane;
5-[(N-(2-((3,5-bis(trifluoromethyl)phenyl)methyloxy)-1-phenylethyl)-N-methylamino)methyl] -2,3-dihydro-4H-1,2,4-triazol- 3-one;
5-[(N-(2-((3,5-bis(trifluoromethyl)phenyl)methyloxy)-1-phenylethyl)ammonium)methyl] -2,3-dihydro-4H-1,2,4-triazol- 3-one;
5-[(N-(2-((((3-t-butyl,5-methyl)phenyl)methyloxy)-1-phenylethyl))-N-methylamino)methyl] -2,3-dihydro-4H-1,2,4-triazol- 3-one;
5-[((N-(1-((3,5-bis(trifluoromethyl)phenyl)methyloxy)- 3,3-diphenylprop-2-yl)-N-methyl)amino)methyl]-2,3-dihydro-4H-1,2,4-triazol-3-one;
5-[(N-(1-((3,5-bis(trifluoromethyl)phenyl)methyloxy)-3,3-diphenylprop- 2-yl)amino)methyl]-2,3-dihydro-4H-1,2,4-triazol- 3-one;
5-[(N-((2S)-2-(1-((3,5-dichlorophenyl)methyloxy))-2-phenyl)ethyl)aminomethyl] -2,3-dihydro-4H-1,2,4-triazol-3one;
(S)-5-[N-(1-(2-((3,5-bis(trifluoromethyl)phenyl) methyloxy)-1-phenyl)ethyl)aminomethyl]imidazolidine-2,4-dione;
(S)-3-[N-(1-(2-((3,5-bis(trifluoromethyl)phenyl) methyloxy)-1-phenyl)ethyl)-N-methylaminomethyl]-1,2,4-triazole;
(S)-5-[N-(1-(2-((3,5-bis(trifluoromethyl)phenyl) methyloxy)-1-phenyl)ethyl)-N-ethylaminomethyl]-2,3-dihydro-4H-1,2,4-triazol-3-one;
(S)-5-[N-(1-(2-((3,5-bis(trifluoromethyl)phenyl) methyloxy)-1-phenyl)ethyl)-N-propylaminomethyl]-2,3-dihydro-4H-1,2,4-triazol-3-one;
(R)-5-[N-(1-(2-((3,5-bis(trifluoromethyl)phenyl) methyloxy)-1-phenyl)ethyl)-N-ethylaminomethyl]-2,3-dihydro-4H-1,2,4-triazol-3-one;
(S)-3-[1-[N-(1-(2-((3,5-bis(trifluoromethyl)phenyl) methyloxy)-1-phenyl)ethyl)-N-ethylamino]ethyl]-1,2,4-triazole;
(S)-5-[N-(1-(2-((3,5-bis(trifluoromethyl)phenyl) methyloxy)-1-phenyl)ethyl)aminomethyl]tetrazole;
(S)-5-[N-(1-(2-((3,5-bis(trifluoromethyl)phenyl) methyloxy)-1-phenyl)ethyl)aminomethyl]-2-N-methyltetrazole;
(S)-5-[N-(1-(2-((3,5-bis(trifluoromethyl)phenyl) methyloxy)-1-phenyl)ethyl)aminomethyl]-1-N-methyltetrazole;
(S)-5-[N-(1-(2-((3,5-bis(trifluoromethyl)phenyl) methyloxy)-1-phenyl)ethyl)-N-methylaminomethyl]tetrazole;
5-[N-(1-(2-((3,5-bis(trifluoromethyl)phenyl)methyloxy)-1-phenyl)ethyl)-N-methylaminomethyl)- 2-N-methyltetrazole;
(S)-5-[N-(1-(2-((3,5-bis(trifluoromethyl)phenyl) methyloxy)-1-phenyl)ethyl)-N-methylaminomethyl]-1-N-methyltetrazole;
(R)-5-[N-(1-(2-((3,5-bis(trifluoromethyl)phenyl) methyloxy)-1-phenyl)ethyl)-N-methylaminomethyl]tetrazole;
(R)-5-[N-(1-(2-((3,5-bis(trifluoromethyl)phenyl) methyloxy)-1-phenyl)ethyl)-N-methylaminomethyl]-2-N-methyltetrazole;
(R)-5-[N-(1-(2-((3,5-bis(trifluoromethyl)phenyl) methyloxy)-1-phenyl)ethyl)-N-methylaminomethyl]-1-N-methyltetrazole;
(S)-5-[2-[N-(1-(2-((3,5-bis(trifluoromethyl)phenyl) methyloxy)-1-phenyl)ethyl)-N-methylamino]ethyl]tetrazole;
(S)-5-[N-((2-(((3-chloro-5-methyl)phenyl)methyloxy)-1-phenyl)ethyl)-N-methylaminomethyl -2,3-dihydro-4H-1,2, 4-triazol- 3-one;
(S)-5-[N-[1-((3,5-bis(trifluoromethyl)phenyl)methyloxy)-3,3-diphenylprop-2-yl]-N-methylaminomethyl]-2,3-dihydro- 4H-1,2,4-triazol-3-one;
(R)-5-[N-[1-((3,5-bis(trifluoromethyl)phenyl)methyloxy)-3,3-diphenylprop-2-yl]-N-methylaminomethyl]-2,3-dihydro- 4H-1,2,4-triazol-3-one;
5-[N-[1-((3,5-bis(trifluoromethyl)phenyl)methyloxy)-3,3-diphenylprop- 2-yl]-N-ethylaminomethyl]-2,3-dihydro-4H-1,2,4-triazol-3-one;
5-[N-[1-((3,5-bis(trifluoromethyl)phenyl)methyloxy)-3,3-diphenylprop- 2-yl]-N-methylaminomethyl]-N-methyl-2,3-dihydro- 4H-1,2,4-triazol-3-one;

and pharmaceutically acceptable salts and prodrugs thereof.

11. A pharmaceutical composition comprising a compound as claimed in claim 1 in association with a pharmaceutically acceptable carrier.

12. A method for the treatment of a physiological disorder associated with an excess of tachykinins, which method comprises administration to a patient in need thereof of a tachykinin-reducing amount of a compound according to claim 1.

13. A method according to claim 12 for the treatment of pain or inflammation.

14. A method according to claim 12 for the treatment of migraine.

15. A method according to claim 12 for the treatment of arthritis.

* * * * *